US008329601B2

United States Patent
Shi et al.

(10) Patent No.: US 8,329,601 B2
(45) Date of Patent: *Dec. 11, 2012

(54) BIODEGRADABLE AND RENEWABLE FILM

(75) Inventors: Bo Shi, Neenah, WI (US); Sarah A. Funk, Omro, WI (US); James H. Wang, Appleton, WI (US); Gregory J. Wideman, Menasha, WI (US); Ross T. Kaufman, Neenah, WI (US); Vasily A. Topolkaraev, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 927 days.

This patent is subject to a terminal disclaimer.

(21) Appl. No.: 12/337,779

(22) Filed: Dec. 18, 2008

(65) Prior Publication Data

US 2010/0159203 A1    Jun. 24, 2010

(51) Int. Cl.
*B32B 27/00* (2006.01)
*B32B 27/12* (2006.01)
*C08L 89/00* (2006.01)
*B29C 65/00* (2006.01)
*B29C 47/00* (2006.01)

(52) U.S. Cl. ........ 442/159; 428/220; 524/498; 442/394; 264/41; 264/210.6

(58) Field of Classification Search .................. 428/159, 428/220; 524/498; 442/394; 264/41, 210.6
See application file for complete search history.

(56) References Cited

U.S. PATENT DOCUMENTS

| 3,137,592 A | 6/1964 | Protzman et al. |
| 3,655,129 A | 4/1972 | Seiner |

(Continued)

FOREIGN PATENT DOCUMENTS

EP    0565386 A1    10/1993

(Continued)

OTHER PUBLICATIONS

Abstract of Japanese Patent No. JP2006137847 dated Jun. 1, 2006, 1 page.

(Continued)

*Primary Examiner* — Rena Dye
*Assistant Examiner* — Susan R Dye
(74) *Attorney, Agent, or Firm* — Dority & Manning, P.A.

(57) ABSTRACT

A biodegradable and renewable film that may be employed in a wide variety of applications is provided. The film is formed from a thermoplastic composition that contains at least one starch and at least one plant protein. Even at a high renewable material content, the present inventors have discovered that films may be readily formed from plant proteins and starches by selectively controlling the individual amount of the starch and plant proteins, the nature of the starch and plant proteins, and other components used in the film. Balancing the amount of starches and plant proteins within a certain range, for instance, can reduce the likelihood of plant protein aggregation and enhance the ability of the composition to be melt processed. The composition also contains at least one plasticizer that improves the thermoplastic nature of the protein and starch components. The selection of the plasticizer may also help reduce the tendency of the plant protein to aggregate during melt processing. For example, a relatively acidic plasticizer (e.g., carboxylic acid) may be employed in certain embodiments to minimize the formation of disulfide bonds in a gluten protein, and thereby decrease its tendency to aggregate.

30 Claims, 3 Drawing Sheets

U.S. PATENT DOCUMENTS

| | | |
|---|---|---|
| 3,963,656 A | 6/1976 | Meisert et al. |
| 4,174,330 A | 11/1979 | Gilbert et al. |
| 4,209,417 A | 6/1980 | Whyte |
| 4,797,468 A | 1/1989 | De Vries |
| 5,028,648 A | 7/1991 | Famili et al. |
| 5,028,658 A | 7/1991 | David et al. |
| 5,093,422 A | 3/1992 | Himes |
| 5,102,465 A | 4/1992 | Lamond |
| 5,169,706 A | 12/1992 | Collier, IV et al. |
| 5,292,783 A | 3/1994 | Buchanan et al. |
| 5,382,611 A | 1/1995 | Stepto et al. |
| 5,397,834 A | 3/1995 | Jane et al. |
| 5,446,079 A | 8/1995 | Buchanan et al. |
| 5,470,944 A | 11/1995 | Bonsignore |
| 5,523,293 A | 6/1996 | Jane et al. |
| 5,525,281 A | 6/1996 | Lorcks et al. |
| 5,559,171 A | 9/1996 | Buchanan et al. |
| 5,580,911 A | 12/1996 | Buchanan et al. |
| 5,599,858 A | 2/1997 | Buchanan et al. |
| 5,605,961 A | 2/1997 | Lee et al. |
| 5,641,562 A | 6/1997 | Larson et al. |
| 5,665,152 A | 9/1997 | Bassi et al. |
| 5,747,648 A | 5/1998 | Bassi et al. |
| 5,770,682 A | 6/1998 | Ohara et al. |
| 5,817,721 A | 10/1998 | Warzelhan et al. |
| 5,821,327 A | 10/1998 | Oota et al. |
| 5,880,254 A | 3/1999 | Ohara et al. |
| 5,900,322 A | 5/1999 | Buchanan et al. |
| 5,910,545 A | 6/1999 | Tsai et al. |
| 5,922,379 A | 7/1999 | Wang |
| 5,939,192 A | 8/1999 | Rettenbacher et al. |
| 5,945,480 A | 8/1999 | Wang et al. |
| 5,965,708 A | 10/1999 | Bassi et al. |
| 5,977,312 A | 11/1999 | Bassi et al. |
| 5,981,012 A | 11/1999 | Pomplun et al. |
| 5,985,396 A | 11/1999 | Kerins et al. |
| 6,008,276 A | 12/1999 | Kalbe et al. |
| 6,020,425 A | 2/2000 | Wang et al. |
| 6,063,866 A | 5/2000 | Wang et al. |
| 6,075,118 A | 6/2000 | Wang et al. |
| 6,096,809 A | 8/2000 | Lorcks et al. |
| 6,135,987 A | 10/2000 | Tsai et al. |
| 6,225,388 B1 | 5/2001 | Tsai et al. |
| 6,231,970 B1 | 5/2001 | Andersen et al. |
| 6,235,816 B1 | 5/2001 | Lorcks et al. |
| 6,258,924 B1 | 7/2001 | Warzelhan et al. |
| 6,296,914 B1 | 10/2001 | Kerins et al. |
| 6,297,347 B1 | 10/2001 | Warzelhan et al. |
| 6,326,458 B1 | 12/2001 | Gruber et al. |
| 6,350,518 B1 | 2/2002 | Schertz et al. |
| 6,369,215 B1 | 4/2002 | Peltonen et al. |
| 6,414,108 B1 | 7/2002 | Warzelhan et al. |
| 6,417,312 B1 | 7/2002 | Kirchmeyer et al. |
| 6,469,099 B1 | 10/2002 | Farah et al. |
| 6,517,625 B2 | 2/2003 | Bassi et al. |
| 6,530,910 B1 | 3/2003 | Pomplun et al. |
| 6,544,455 B1 | 4/2003 | Tsai et al. |
| 6,552,124 B2 | 4/2003 | Wang et al. |
| 6,552,162 B1 | 4/2003 | Wang et al. |
| 6,565,640 B1 | 5/2003 | Bengs et al. |
| 6,573,340 B1 * | 6/2003 | Khemani et al. .............. 525/437 |
| 6,605,367 B2 | 8/2003 | Bassi et al. |
| 6,605,657 B1 | 8/2003 | Favis et al. |
| 6,660,211 B2 | 12/2003 | Topolkaraev et al. |
| 6,676,984 B1 | 1/2004 | Sharp et al. |
| 6,703,115 B2 | 3/2004 | Hale et al. |
| 6,709,671 B2 | 3/2004 | Zerbe et al. |
| 6,713,595 B2 | 3/2004 | Chung et al. |
| 6,746,705 B2 | 6/2004 | Altieri et al. |
| 6,749,795 B2 | 6/2004 | Murphy |
| 6,767,961 B1 | 7/2004 | Wang et al. |
| 6,806,353 B2 | 10/2004 | Zhang et al. |
| 6,838,403 B2 | 1/2005 | Tsai et al. |
| 6,890,989 B2 | 5/2005 | Wang et al. |
| 6,905,759 B2 | 6/2005 | Topolkaraev et al. |
| 6,921,581 B2 | 7/2005 | Van Gelder et al. |
| 6,933,335 B1 | 8/2005 | Berger et al. |
| 6,946,506 B2 | 9/2005 | Bond et al. |
| 6,958,371 B1 | 10/2005 | Wang et al. |
| 6,984,426 B2 | 1/2006 | Miksic et al. |
| 6,987,138 B2 | 1/2006 | Tokiwa et al. |
| 7,045,650 B2 | 5/2006 | Lawrey et al. |
| 7,053,151 B2 | 5/2006 | Wang et al. |
| 7,077,994 B2 | 7/2006 | Bond et al. |
| 7,098,292 B2 | 8/2006 | Zhao et al. |
| 7,124,450 B2 | 10/2006 | Davidson |
| 7,153,354 B2 | 12/2006 | Narayan et al. |
| 7,153,569 B2 | 12/2006 | Kaufman et al. |
| 7,235,594 B2 | 6/2007 | Han et al. |
| 7,297,394 B2 | 11/2007 | Khemani et al. |
| 7,307,125 B2 | 12/2007 | Chundury et al. |
| 7,368,160 B2 | 5/2008 | Inglis |
| 7,402,618 B2 | 7/2008 | Xu |
| 7,413,731 B2 | 8/2008 | Heltovics et al. |
| 2002/0098341 A1 | 7/2002 | Schiffer et al. |
| 2003/0077395 A1 | 4/2003 | Bassi et al. |
| 2003/0099692 A1 | 5/2003 | Lydzinski et al. |
| 2003/0232933 A1 | 12/2003 | Lagneaux et al. |
| 2004/0034149 A1 | 2/2004 | Garcia |
| 2004/0108611 A1 | 6/2004 | Dennis et al. |
| 2005/0186256 A1 | 8/2005 | Dihel et al. |
| 2005/0208294 A1 | 9/2005 | Kaufman et al. |
| 2005/0244606 A1 | 11/2005 | Egawa |
| 2006/0135728 A1 | 6/2006 | Peerlings et al. |
| 2006/0149199 A1 | 7/2006 | Topolkaraev et al. |
| 2007/0031555 A1 | 2/2007 | Axelrod et al. |
| 2007/0049685 A1 | 3/2007 | Hansel et al. |
| 2007/0049719 A1 | 3/2007 | Brauer et al. |
| 2007/0129467 A1 | 6/2007 | Scheer |
| 2007/0246867 A1 | 10/2007 | Nelson et al. |
| 2007/0298237 A1 | 12/2007 | Goino et al. |
| 2008/0038496 A1 | 2/2008 | Bastioli et al. |
| 2008/0147034 A1 | 6/2008 | Wang et al. |
| 2009/0054548 A1 | 2/2009 | Wang et al. |

FOREIGN PATENT DOCUMENTS

| | | |
|---|---|---|
| EP | 1235879 B1 | 5/2001 |
| EP | 1075188 B1 | 11/2005 |
| WO | WO 0136535 A1 | 5/2001 |
| WO | WO 02053376 A2 | 7/2002 |
| WO | WO 02053376 A3 | 7/2002 |
| WO | WO 2005113616 A2 | 12/2005 |
| WO | WO 2005113616 A3 | 12/2005 |

OTHER PUBLICATIONS

Abstract of Japanese Patent No. JP2006505719 dated Feb. 16, 2006, 1 page.

ASTM D 1238-04c—*Standard Test Method for Melt Flow Rates of Thermoplastics by Extrusion Plastometer*, Current edition approved Dec. 1, 2004, Originally approved in 1965, pp. 1-14.

ASTM D 1343-56—*Standard Method of Test for Viscosity of Cellulose Derivatives by Ball-Drop Method*, Adopted 1956, pp. 486-489.

ASTM D 1505-03—*Standard Test Method for Density of Plastics by the Density-Gradient Technique*, Current edition approved Nov. 1, 2003, Originally approved in 1957, pp. 1-7.

ASTM D 1525-07—*Standard Test Method for Vicat Softening Temperature of Plastics*, Current edition approved Mar. 1, 2007, Originally approved in 1958, pp. 1-9.

ASTM D 3418-03 (D 3417-99)—*Standard Test Method for Transition Temperatures and Enthalpies of Fusion and Crystallization of Polymers by Differential Scanning Calorimetry*, Current edition approved Dec. 1, 2003, Originally approved in 1976, pp. 66-72.

ASTM D 3806-98 (Reapproved 2004)—*Standard Test Method of Small-Scale Evaluation of Fire-Retardant Paints (2-Foot Tunnel Method)*, Current edition approved Jun. 1, 2004, Originally approved in 1979, pp. 1-6.

ASTM D 5034-95—*Standard Test Method for Breaking Strength and Elongation of Textile Fabrics (Grab Test)*, Current edition approved May 15, 1995, pp. 674-681.

ASTM D 5338-92—*Standard Test Method for Determining Aerobic Biodegradation of Plastic Materials Under Controlled Composting Conditions*, Current edition approved Dec. 15, 1992, pp. 456-461.

ASTM D 638-08—*Standard Test Method for Tensile Properties of Plastics*, Current edition approved Apr. 1, 2008, Originally approved in 1941, pp. 1-16.

ASTM D 790-99—*Standard Test Methods for Flexural Properties of Unreinforced and Reinforced Plastics and Electrical Insulating Materials*, Current edition approved Nov. 10, 1999, pp. 150-158.

Article—*Aging Properties of Films of Plasticized Vital Wheat Gluten Cast from Acidic and Basic Solutions*, Olabarrieta et al., Biomacromolecules, vol. 7, No. 5, 2006, pp. 1657-1664.

Article—*Biodegradable Compositions by Reactive Processing of Aliphatic Polyester/Polysaccharide Blends*, Dubois et al., Macromol. Symp., vol. 198, 2003, pp. 233-243.

Article—*Biodegradable Soy Protein-Polyester Blends by Reactive Extrusion Process*, Graiver et al., Journal of Applied Polymer Science, vol. 92, 2004, pp. 3231-3239.

Article—*Chemical Modification of Starch*, Tomasik et al., Advances in Carbohydrate Chemistry and Biochemistry, vol. 59, 2004, pp. 175-316.

Article—*Edible Protein Films and Coatings*, Food Proteins and Their Applications edited by S. Damodaran and a. Paraf, John M. Krochta, 1997, pp. 529-539.

Article—*Effects of Extruder Die Nozzle Dimensions on Expansion and Micrographic Characterization During Extrusion of Acetylated Starch*, Ganjyal et al., Starch/Starke, vol. 56, 2004, pp. 108-117.

Article—*Extrusion of Wheat Gluten Plasticized with Glycerol: Influence of Process Conditions on Flow Behavior, Rheological Properties and Molecular Size Distribution*, Redl et al., Cereal Chemistry, vol. 76, No. 3, 1999, pp. 361-370.

Article—*Glycol Glucosides from Starch by Continuous Twin-Screw Extruder Processing*, Carr et al., Cereal Chemistry, vol. 66, No. 3, 1989, pp. 238-243.

Article—*Heat and shear mediated polymerization of plasticized wheat gluten protein upon mixing*, Redl et al., Journal of Cereal Science 38, 2003, pp. 105-114.

Article—*Polyurethane/Polyolefin Blends: Morphology, Compatibilization and Mechanical Properties*, Wang et al., Polymers & Polymer Composites, vol. 14, No. 1, 2006, 11 pages.

Article—*Preparation of Acetylated Distarch Adipates by Extrusion*, Mail et al., Lebensmittel-Wissenschaft und-Technologie, vol. 34, No. 6, 2001, pp. 384-389.

Article—*Reactivity of Wheat Gluten Protein during Mechanical Mixing: Radical and Nucleophilic Reactions for the Addition of Molecules on Sulfur*, Auvergne et al., Biomacromolecules, vol. 9, No. 2, 2008, pp. 664-671.

Article—*Soy Protein-Based Biodegradable Plastics*, Mungara et al., Proceedings in Plastics Impact on the Environment Conference, Society of Plastic, Feb. 2003, pp. 393-397.

Article—*Starch Modification, Destruction and Hydrolysis during O-Formylation*, Divers et al., Starch/Stärke 56, 2004, pp. 389-398.

Article—*The chemical modification of a range of starches under aqueous reaction conditions*, Fang et al., Carbohydrate Polymers 55, 2004, pp. 283-289.

Article—*The History of Tomorrow's Materials: Protein-Based Biopolymers*, Ralston et al., Plastics Engineering, Feb. 2008, pp. 36-40.

Article—*The Hydroxypropylation of Starch in a Self-Wiping Twin Screw Extruder*, De Graaf et al., Advances in Polymer Technology, vol. 22, No. 1, 2003, pp. 56-68.

Article—*Thermoplastic Processing of Protein-Based Bioplastics: Chemical Engineering Aspects of Mixing, Extrusion and Hot Molding*, Pommet et al., Macromol. Symp., vol. 197, 2003, pp. 207-217.

Article—*Thermoplastic Processing of Proteins for Film Formation—A Review*, Hernandez-Izquierdo et al., Journal of Food Science, vol. 73, No. 2, 2008, pp. R30-R39.

Related U.S. Patent Applications.

Abstract of Japanese Patent No. JP2001 509525 dated Jul. 24, 2001, 1 page.

Abstract of Korean Patent No. KR1020060132998 dated Dec. 22, 2006, 1 page.

Search Report and Written Opinion for PCT/IB2009/054732 dated Jun. 18, 2010, 15 pages.

* cited by examiner

BIODEGRADABLE AND RENEWABLE FILM

BACKGROUND OF THE INVENTION

Thermoplastic films are used in a wide variety of products to accomplish various functions. For example, breathable films are often employed in disposable absorbent articles (e.g., diapers, feminine hygiene products, incontinence products, etc.) that allow the passage of vapor through the diaper and into the environment while holding liquid. The film contains a filler (e.g., calcium carbonate) that causes a series of micropores to develop in the film when stretched. One shortcoming with these and other films is that they are generally formed from polyolefins (e.g., LLDPE), which are not biodegradable. Consequently, various attempts have been made to form films from a biodegradable polymer, such as an aliphatic-aromatic copolyester. Such attempts, however, were generally designed only for a specific application and lacked the wide range of flexibility in processing and physical properties often needed for films having a large number of potential uses. Further, although biodegradable, the aliphatic-aromatic copolyesters are synthetic and thus not generally renewable. Unfortunately, polymers that are both biodegradable and renewable are often difficult to melt process into a film. Gluten protein, for example, is a biodegradable, renewable plant protein that contains gliadin and glutenin protein components. When processed under temperature and shear, cysteine-rich amino acids present within these protein components can form disulfide inter- and intra-molecular bonds. Such bonds may result in the aggregation of the protein granules, which inhibits the protein from being readily melt processed into a film structure.

As such, a need currently exists for a technique for forming biodegradable, renewable films that may be readily adapted to numerous potential applications.

SUMMARY OF THE INVENTION

In accordance with one embodiment of the present invention, a biodegradable and renewable film is disclosed that comprises a thermoplastic composition. The thermoplastic composition contains a starch component in an amount from about 25 wt. % to about 85 wt. %, a plant protein component in an amount from about 5 wt. % to about 50 wt. %, and a plasticizer component in an amount from about 5 wt. % to about 50 wt. %. Further, the combined amount of the starch and the plant protein in the thermoplastic composition is about 40 wt. % or greater.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
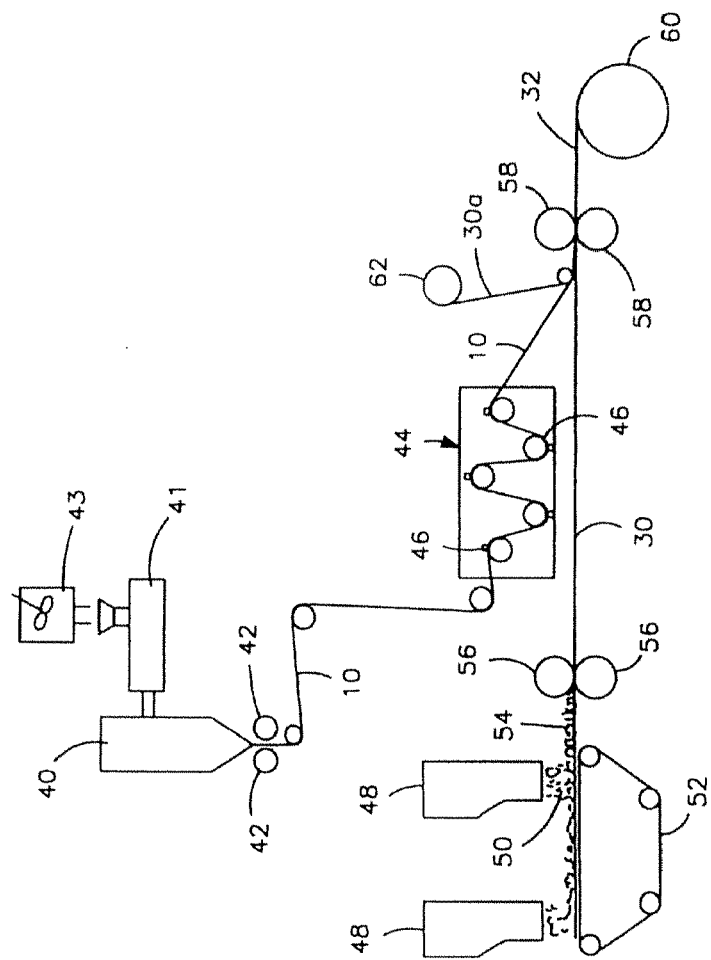
FIG. 1 is a schematic illustration of one embodiment of a method for forming a film and film/nonwoven laminate.

Repeat use of references characters in the present specification and drawings is intended to represent same or analogous features or elements of the invention.

DETAILED DESCRIPTION OF REPRESENTATIVE EMBODIMENTS

Definitions

As used herein, the term "biodegradable" generally refers to a material that degrades from the action of naturally occurring microorganisms, such as bacteria, fungi, and algae; environmental heat; moisture; or other environmental factors. If desired, the extent of biodegradability may be determined according to ASTM Test Method 5338.92.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

The present invention is directed to a biodegradable and renewable film that may be employed In a wide variety of applications. The film is formed from a thermoplastic composition that contains at least one starch and at least one plant protein. To optimize the renewability of the film, the combined amount of starch(es) and plant protein(s) in the composition is relatively high, such as about 40 wt. % or greater, in some embodiments from about 50 wt. % to about 95 wt. %, and in some embodiments, from about 60 wt. % to about 90 wt. %. Even at such a high content, however, the present inventors have discovered that films may be readily formed from plant proteins and starches by selectively controlling the individual amount of the starch and plant proteins, the nature of the starch and plant proteins, and other components used in the film. In this regard, the thermoplastic composition used to form the film contains a starch component in an amount from about 25 wt. % to about 85 wt. %, in some embodiments, from about 30 wt. % to about 80 wt. %, and in some embodiments, from about 40 wt. % to about 70 wt. % and a plant protein component in an amount from about 5 wt. % to about 50 wt. %, in some embodiments, from about 10 wt. % to about 40 wt. %, and in some embodiments, from about 15 wt. % to about 35 wt. %.

Balancing the amount of starches and plant proteins within the ranges described above can reduce the likelihood of plant protein aggregation and enhance the ability of the composition to be melt processed. The composition also contains a plasticizer component in an amount from about 5 wt. % to about 50 wt. %, in some embodiments, from about 10 wt. % to about 40 wt. %, and in some embodiments, from about 15 wt. % to about 35 wt. % of the composition. The plasticizer improves the thermoplastic nature of the protein and starch components. The selection of the plasticizer may also help reduce the tendency of the plant protein to aggregate during melt processing. For example, a relatively acidic plasticizer (e.g., carboxylic acid) may be employed in certain embodiments to minimize the formation of disulfide bonds in a gluten protein, and thereby decrease its tendency to aggregate.

Various embodiments of the present invention will now be described in more detail below.

I. Thermoplastic Composition

A. Starch Component

Starch is a natural polymer composed of amylose and amylopectin. Amylose is essentially a linear polymer having a molecular weight in the range of 100,000-500,000, whereas amylopectin is a highly branched polymer having a molecular weight of up to several million. Although starch is produced in many plants, typical sources include seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. To facilitate the formation of films in accordance with the present invention, the starch may be chemically modified by processes known in the art (e.g., esterification, etherification, oxidation, acid hydrolysis, enzymatic hydrolysis, etc.). Starch ethers and/or esters may be particularly desirable, such as hydroxyalkyl starches, carboxymethyl starches, etc. The hydroxyalkyl group of hydroxyalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. Examples of such starch esters may include starch acetate, starch butyrate, starch alkanoate, etc. The degree of esterification may vary as desired, such as from 1 to 3 ester groups per glucosidic unit of the starch.

The starch may contain different weight percentages of amylose and amylopectin, different polymer molecular weights, etc. High amylose starches contain greater than about 50% by weight amylose and low amylose starches contain less than about 50% by weight amylose. Although not required, low amylose starches having an amylose content of from about 10% to about 40% by weight, and in some embodiments, from about 15% to about 35% by weight, are particularly suitable for use in the present invention. Examples of such low amylose starches include corn starch and potato starch, both of which have an amylose content of approximately 20% by weight. Such low amylose starches typically have a number average molecular weight ("$M_n$") ranging from about 50,000 to about 1,000,000 grams per mole, in some embodiments from about 75,000 to about 800,000 grams per mole, and in some embodiments, from about 100,000 to about 600,000 grams per mole, as well as a weight average molecular weight ("$M_w$") ranging from about 5,000,000 to about 25,000,000 grams per mole, in some embodiments from about 5,500,000 to about 15,000,000 grams per mole, and in some embodiments, from about 6,000,000 to about 12,000,000 grams per mole. The ratio of the weight average molecular weight to the number average molecular weight ("$M_w/M_n$"), i.e., the "polydispersity index", is also relatively high. For example, the polydispersity index may range from about 20 to about 100. The weight and number average molecular weights may be determined by methods known to those skilled in the art.

B. Plant Protein Component

The protein may be any known in the art and be available as part of a larger formulation, such as an isolate with carbohydrates and fiber. Plant proteins may include, for instance, water-insoluble fractions from zein, corn gluten, wheat gluten, canola, sunflower, sorghum, and soybean. Any form of protein may be used, such as isolates, concentrates and flour. For example, soy proteins may be in the form of an isolate containing from about 75 wt. % to about 98 wt. % protein, a concentrate containing from about 50 wt. % to about 75 wt. % protein, or flour containing from about 30 wt. % to about 50 wt. % protein. In certain embodiments, it is desirable to use a protein that is relatively pure, such as those having a protein content of about 75 wt. % or more, and in some cases, about 85 wt. % or more. Gluten proteins, for instance, may be purified by washing away any associated starch to leave a composite of gliadin and glutenin proteins. Examples of such proteins are available from Archer Daniels Midland ("ADM") of Decatur, Ill. Similarly, purified soy protein isolates may be prepared by alkaline extraction of a defatted meal and acid precipitation, a technique well-known and used routinely in the art. Such purified soy proteins are commercially available as Promine R (Central Soya), which is a soy protein isolate having a protein content of approximately 95 wt. %. Other purified soy protein products are also available from DuPont of Louisville, Ky. under the designation PRO-Cote®.

C. Plasticizer Component

In addition to starch(es) and plant protein(s), plasticizer(s) may also be employed in the thermoplastic composition to help render the starch and/or plant protein melt-processable. Starches, for instance, normally exist in the form of granules that have a coating or outer membrane that encapsulates the more water-soluble amylose and amylopectin chains within the interior of the granule. When heated, plasticizers may soften and penetrate the outer membrane and cause the inner starch chains to absorb water and swell. This swelling will, at some point, cause the outer shell to rupture and result in an irreversible destructurization of the starch granule. Once destructurized, the starch polymer chains containing amylose and amylopectin polymers, which are initially compressed within the granules, will stretch out and form a generally disordered intermingling of polymer chains. Upon resolidification, however, the chains may reorient themselves to form crystalline or amorphous solids having varying strengths depending on the orientation of the starch polymer chains.

Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds which do not have hydroxyl groups, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic carboxylic acids may also be used, such as lactic acid, maleic acid, acrylic acid, copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight plasticizer is preferred, such as less than about 20,000 g/mol, preferably less than about 5,000 g/mol and more preferably less than about 1,000 g/mol.

If desired, the plasticizer may be selected to have a certain pH (refers to the pH prior to incorporation into the thermoplastic composition). For example, as indicated above, plasticizers having a relatively low pH can reduce the tendency of gluten proteins to aggregate during melt processing. Thus, when gluten proteins are employed, a plasticizer may be selected that has a pH of about 6 or less, in some embodiments from about 1 to about 5, and in some embodiments, from about 2 to about 4. Examples of such plasticizers may include aliphatic carboxylic acids, such as lactic acid, maleic acid, acrylic acid, etc. In other embodiments, it may be desirable to use plasticizers having a higher pH, such as when the plant protein is not generally sensitive to pH. For example, soy proteins generally lack the cysteine residues that lead to aggregation in gluten proteins. Thus, when employed, the soy protein may be used with plasticizers having a relatively wide range of pH levels. One example of such a plasticizer is glycerol, which has a pH of about 6.

D. Other Optional Components

It should be understood that other components may also be included in the thermoplastic composition. One such component that may be employed is a biodegradable polyester to aid in the film formation process, including aliphatic polyesters, such as polycaprolactone, polyesteramides, modified polyethylene terephthalate, polylactic acid (PLA) and its copolymers, terpolymers based on polylactic acid, polyglycolic acid, polyalkylene carbonates (such as polyethylene carbonate), poly-3-hydroxybutyrate (PHB), poly-3-hydroxyvalerate (PHV), poly-3-hydroxybutyrate-co-4-hydroxybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aliphatic-aromatic copolyesters, and so forth. When employed, the content of such polyesters is typically minimized to enhance the renewability of the film. For example, such polyester(s) may constitute from about 0.5 wt. % to about 50 wt. %, in some embodiments from about 1 wt. % to about 40 wt. %, and in some embodiments, from about 2 wt. % to about 30 wt. % of the thermoplastic composition.

Aliphatic-aromatic copolyesters, for instance, may be employed in the composition that are synthesized using any known technique, such as through the condensation polymerization of a polyol In conjunction with aliphatic and aromatic dicarboxylic acids, esters, or anhydrides thereof. The polyols may be substituted or unsubstituted, linear or branched, polyols selected from polyols containing 2 to about 12 carbon atoms and polyalkylene ether glycols containing 2 to 8 carbon atoms. Examples of polyols that may be used include, but are not limited to, ethylene glycol, diethylene glycol, propylene glycol, 1,2-propanediol, 1,3-propanediol, 2,2-dimethyl-1,3-propanediol, 1,2-butanediol, 1,3-butanediol, 1,4-butanediol, 1,2-pentanediol, 1,5-pentanediol, 1,6-hexanediol, polyethylene glycol, diethylene glycol, 2,2,4-trimethyl-1,6-hexanediol, thiodiethanol, 1,3-cyclohexanedimethanol, 1,4-cyclohexanedimethanol, 2,2,4,4-tetramethyl-1,3-cyclobutanediol, cyclopentanediol, triethylene glycol, and tetraethylene glycol. Preferred polyols include 1,4-butanediol; 1,3-propanediol; ethylene glycol; 1,6-hexanediol; diethylene glycol; and 1,4-cyclohexanedimethanol.

The aromatic dicarboxylic acid may include, for instance, terephthalic acid phthalic acid, isophthalic acid, etc., and derivatives thereof, including esters (e.g., monoesters, diesters, etc.), anhydrides (e.g., terephthalic anhydride), and so forth. Suitable esters of terephthalic acid may include alkyl, cycloalkyl and alkoxyalkyl terephthalates, where the alkyl, cycloalkyl and alkoxyalkyl groups generally have from 1 to 30, preferably from 2 to 20 and particularly preferably from 3 to 18, carbon atoms and may be branched or linear. Examples of suitable alkyl terephthalates include, for instance, monomethyl terephthalate, dimethyl terephthalate, diethyl terephthalate, di-n-propyl terephthalate, di-n-butyl terephthalate, di-tert-butyl terephthalate, diisobutyl terephthalate, monoglycol esters of terephthalic acid, diglycol esters of terephthalic acid, di-n-octyl terephthalate, diisooctyl terephthalate, mono-2-ethylhexyl terephthalate, di-2-ethylhexyl terephthalate, di-n-nonyl terephthalate, diisononyl terephthalate, di-n-decyl terephthalate, di-n-undecyl terephthalate, diisodecyl terephthalate, diisoundecyl terephthalate, diisododecyl terephthalate, di-n-octadecyl terephthalate, diisooctadecyl terephthalate, di-n-eicosyl terephthalate, ditridecyl terephthalate, diisotridecyl terephthalate, monocyclohexyl terephthalate, dicyclohexyl terephthalate, etc. Suitable esters of phthalic and/or isophthalic acid may include alkyl, cycloalkyl and alkoxyalkyl phthalates and/or isophthalates, where the alkyl, cycloalkyl and alkoxyalkyl groups generally have from 1 to 30, preferably from 2 to 20 and particularly preferably from 3 to 18, carbon atoms and may be branched or linear. Examples of suitable alkyl phthalates include, for instance, monomethyl phthalate, dimethyl phthalate, diethyl phthalate, di-n-propyl phthalate, di-n-butyl phthalate, di-tert-butyl phthalate, diisobutyl phthalate, monoglycol esters of phthalic acid, diglycol esters of phthalic acid, di-n-octyl phthalate, diisooctyl phthalate, di-2-ethylhexyl phthalate, di-n-nonyl phthalate, diisononyl phthalate, di-n-decyl phthalate, diisodecyl phthalate, di-n-undecyl phthalate, di-isoundecyl phthalate, diisododecyl phthalate, di-n-octadecyl phthalate, diisooctadecyl phthalate, di-n-eicosyl phthalate, monocyclohexyl phthalate, dicyclohexyl phthalate, etc. Likewise, suitable isophthalates may include monomethyl isophthalate, dimethyl isophthalate, diethyl isophthalate, di-n-propyl isophthalate, di-n-butyl isophthalate, di-tert-butyl isophthalate, diisobutyl isophthalate, monoglycol esters of isophthalic acid, diglycol esters of isophthalic acid, di-n-octyl isophthalate, diisooctyl isophthalate, di-2-ethylhexyl isophthalate, di-n-nonyl isophthalate, diisononyl isophthalate, di-n-decyl isophthalate, diisodecyl isophthalate, di-n-undecyl isophthalate, di-isoundecyl isophthalate, diisododecyl isophthalate, di-n-octadecyl isophthalate, diisooctadecyl isophthalate, di-n-eicosyl isophthalate, monocyclohexyl isophthalate, dicyclohexyl isophthalate, and so forth.

Non-limiting examples of aliphatic dicarboxylic acids include malonic, malic, succinic, oxalic, glutaric, adipic, pimelic, azelaic, sebacic, fumaric, 2,2-dimethyl glutaric, suberic, 1,3-cyclopentanedicarboxylic, 1,4-cyclohexanedicarboxylic, 1,3-cyclohexanedicarboxylic, diglycolic, itaconic, maleic, and 2,5-norbornanedicarboxylic. Representative aromatic dicarboxylic acids that may be used include substituted and unsubstituted, linear or branched, aromatic dicarboxylic acids selected from aromatic dicarboxylic acids containing 8 or more carbon atoms, and derivatives thereof. Non-limiting examples of aromatic dicarboxylic acids include terephthalic acid, isophthalic acid, phthalic acid, naphthalic acid, as well as derivatives thereof, such as dimethyl terephthalate, dimethyl isophthalate, 2,6-napthalene dicarboxylic acid, dimethyl-2,6-naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), etc., and mixtures thereof.

The aromatic dicarboxylic acid monomer constituent may be present in the copolyester in an amount of from about 10 mole % to about 45 mole %, in some embodiments from about 15 mole % to about 35 mole %, and in some embodiments, from about 15 mole % to about 30 mole %. The aliphatic dicarboxylic acid monomer constituent may likewise be present in the copolyester in an amount of from about 15 mole % to about 45 mole %, in some embodiments from about 20 mole % to about 40 mole %, and in some embodiments, from about 25 mole % to about 35 mole %. The polyol monomer constituent may be present in the second copolyester in an amount of from about 30 mole % to about 65 mole %, in some embodiments from about 40 mole % to about 50 mole %, and in some embodiments, from about 45 mole % to about 55 mole %.

If desired, a diisocyanate chain extender may be reacted with the copolyester to increase its molecular weight. Representative diisocyanates may include toluene 2,4-diisocyanate, toluene 2,6-diisocyanate, 2,4'-diphenylmethane diisocyanate, naphthylene-1,5-diisocyanate, xylylene diisocyanate, hexamethylene diisocyanate ("HMDI"), isophorone diisocyanate and methylenebis(2-isocyanatocyclohexane). Trifunctional isocyanate compounds may also be employed that contain isocyanurate and/or biurea groups with a functionality of not less than three, or to replace the diisocyanate compounds partially by tri- or polyisocyanates. The preferred diisocyanate is hexamethylene diisocyanate. The amount of the chain extender employed is typically from about 0.3 to about 3.5 wt. %, in some embodiments, from about 0.5 to about 2.5 wt. % based on the total weight percent of the polymer.

The copolyesters may either be a linear polymer or a long-chain branched polymer. Long-chain branched polymers are generally prepared by using a low molecular weight branching agent, such as a polyol, polycarboxylic acid, hydroxy acid, and so forth. Representative low molecular weight polyols that may be employed as branching agents include glycerol, trimethylolpropane, trimethylolethane, polyethertriols, 1,2,4-butanetriol, pentaerythritol, 1,2,6-hexanetriol, sorbitol, 1,1,4,4-tetrakis(hydroxymethyl)cyclohexane, tris(2-hydroxyethyl)isocyanurate, and dipentaerythritol. Representative higher molecular weight polyols (molecular weight of 400 to 3000) that may be used as branching agents include triols derived by condensing alkylene oxides having 2 to 3 carbons, such as ethylene oxide and propylene oxide with polyol initiators. Representative polycarboxylic acids that may be used as branching agents include hemimellitic acid, trimellitic (1,2,4-benzenetricarboxylic) acid and anhydride, trimesic (1,3,5-benzenetricarboxylic) acid, pyromellitic acid and anhydride, benzenetetracarboxylic acid, benzophenone tetracarboxylic acid, 1,1,2,2-ethane-tetracarboxylic acid, 1,1,2-ethanetricarboxylic acid, 1,3,5-pentanetricarboxylic acid, and 1,2,3,4-cyclopentanetetracarboxylic acid. Representative hydroxy acids that may be used as branching agents include malic acid, citric acid, tartaric acid, 3-hydroxyglutaric acid, mucic acid, trihydroxyglutaric acid, 4-carboxyphthalic anhydride, hydroxyisophthalic acid, and 4-(beta-hydroxyethyl)phthalic acid. Such hydroxy acids contain a combination of 3 or more hydroxyl and carboxyl groups. Especially preferred branching agents include trimellitic acid, trimesic acid, pentaerythritol, trimethylol propane and 1,2,4-butanetriol.

In one particular embodiment, for example, the aliphatic-aromatic copolyester may comprise the following structure:

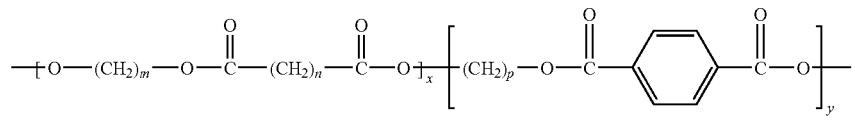

wherein, m is an integer from 2 to 10, in some embodiments from 2 to 4, and in one embodiment, 4;

n is an integer from 0 to 18, in some embodiments from 2 to 4, and in one embodiment, 4;

p is an integer from 2 to 10, in some embodiments from 2 to 4, and in one embodiment, 4;

x is an integer greater than 1, and in some embodiments, from 2 to 100; and y is an integer greater than 1, and in some embodiments from 2 to 100.

One example of such a copolyester is polybutylene adipate terephthalate, which is commercially available under the designation ECOFLEX® F BX 7011 from BASF Corp. Another example of a suitable copolyester containing an aromatic terephthalic acid monomer constituent is available under the designation ENPOL™ 8060M from IRE Chemicals (South Korea). Other suitable aliphatic-aromatic copolyesters may be described in U.S. Pat. Nos. 5,292,783; 5,446,079; 5,559, 171; 5,580,911; 5,599,858; 5,817,721; 5,900,322; and 6,258,924, which are incorporated herein in their entirety by reference thereto for all purposes.

Another suitable aliphatic-aromatic copolyester may comprise the following structure:

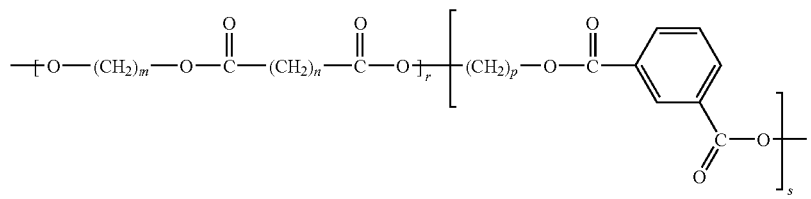

wherein, m is an integer from 2 to 10, in some embodiments from 2 to 4, and in one embodiment, 2;

n is an integer from 0 to 18, in some embodiments from 2 to 4, and in one embodiment, 2;

p is an integer from 2 to 10, in some embodiments from 2 to 4, and in one embodiment, 2;

r is an integer greater than 1, and in some embodiments, from 2 to 100; and s is an integer greater than 1, and in some embodiments, from 2 to 100.

One example of such a copolyester is polyethylene adipate isophthalate, which is commercially available under the designation ECOPOL™ EBP 203, 206F, 1250, or 1306 from Econeer Co., Ltd. (Korea). Another suitable example of such a copolyester is polybutylene adipate isophthalate.

The aliphatic-aromatic copolyester typically has a number average molecular weight ("$M_n$") ranging from about 40,000 to about 20,000 grams per mole, in some embodiments from about 50,000 to about 100,000 grams per mole, and in some embodiments, from about 60,000 to about 85,000 grams per mole. Likewise, the polymer also typically has a weight average molecular weight ("$M_w$") ranging from about 70,000 to about 360,000 grams per mole, in some embodiments from about 80,000 to about 250,000 grams per mole, and in some embodiments, from about 100,000 to about 200,000 grams per mole. The polydispersity index is also relatively low, such as from about 1.0 to about 3.0, in some embodiments from about 1.2 to about 2.0, and in some embodiments, from about 1.4 to about 1.8. The melt flow index of the aromatic-aliphatic polyester may also range from about 0.1 to about 10 grams per 10 minutes, in some embodiments from about 0.5 to about 8 grams per 10 minutes, and in some embodiments, from about 1 to about 5 grams per 10 minutes. The melt flow index is the weight of a polymer (in grams) that may be forced through an extrusion rheometer orifice (0.0825-inch diameter) when subjected to a load of 2160 grams in 10 minutes at a certain temperature (e.g., 190° C.), measured in accordance with ASTM Test Method D1238-E.

The aliphatic-aromatic copolyester also typically has a melting point of from about 40° C. to about 140° C., in some embodiments from about 50° C. to about 130° C., and in some embodiments, from about 60° C. to about 120° C. The glass transition temperature ("$T_g$") of the copolyester is also relatively low to improve flexibility and processability of the polymers. For example, the $T_g$ may be about 25° C. or less, in some embodiments about 0° C. or less, and in some embodiments, about −10° C. or less. The melting temperature and glass transition temperature may be determined using differential scanning calorimetry ("DSC") in accordance with ASTM D-3417.

If desired, dispersion aids may also be employed to help create a uniform dispersion of the starch/protein/plasticizer mixture and retard or prevent separation of the thermoplastic composition into constituent phases. When employed, the dispersion aid(s) typically constitute from about 0.01 wt. % to about 10 wt. %, in some embodiments from about 0.1 wt. % to about 5 wt. %, and in some embodiments, from about 0.5 wt. % to about 4 wt. % of the thermoplastic composition.

Although any dispersion aid may generally be employed in the present invention, surfactants having a certain hydrophilic/lipophilic balance ("HLB") may improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some embodiments of the present invention, the HLB value of the surfactants is from about 1 to about 20, in some embodiments from about 1 to about 15 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

II. Film Construction

The film of the present invention may have a mono-layered or multi-layered structure. Multilayer films normally contain at least one base layer and at least one skin layer, but may contain any number of layers desired. For example, the multilayer film may be formed from a base layer and one or more skin layers, wherein the base layer is formed from the polymer blend of the present invention. The skin layer(s) may be formed from any film-forming polymer. If desired, the skin layer(s) may contain a softer, lower melting polymer or polymer blend that renders the layer(s) more suitable as heat seal bonding layers for thermally bonding the film to a nonwoven web. In most embodiments, the skin layer(s) are formed from a biodegradable polymer. It should be understood, however, that other polymers may also be employed in the skin layer(s), either alone or in conjunction with biodegradable polymers, such as polyolefin polymers (e.g., linear low-density polyethylene (LLDPE), low density polyethylene (LDPE), or polypropylene). The term "linear low density polyethylene" refers to polymers of ethylene and higher alpha olefin comonomers, such as $C_3$-$C_{12}$ and combinations thereof, having a Melt Index (as measured by ASTM D-1238) of from about 0.5 to about 30 grams per 10 minutes at 190° C. Examples of predominately linear polyolefin polymers include, without limitation, polymers produced from the following monomers: ethylene, propylene, 1-butene, 4-methylpentene, 1-hexene, 1-octene and higher olefins as well as copolymers and terpolymers of the foregoing. In addition, copolymers of ethylene and other olefins including butene, 4-methyl-pentene, hexene, heptene, octene, decene, etc., are also examples of predominately linear polyolefin polymers. Additional film-forming polymers that may be suitable for use with the present invention, alone or in combination with other polymers, include ethylene vinyl acetate, ethylene ethyl acrylate, ethylene acrylic acid, ethylene methyl acrylate, ethylene normal butyl acrylate, nylon, ethylene vinyl alcohol, polystyrene, polyurethane, and so forth.

Depending on the intended application, the film may be generally liquid and vapor-impermeable or generally liquid impermeable, yet vapor-permeable (i.e., "breathable"). Breathable films, for example, are often used in absorbent articles (e.g., outer cover) in which it is desired to allow moisture to escape from the absorbent core through the film. Similarly, bandages or wound dressings often employ breathable films that allow the release of moisture from the skin at the wound site. Breathable films may be formed with the use of a filler, such as described above. Filled films may be made breathable by stretching, which causes the polymer to break away from the filler and create microporous passageways. Techniques for forming microporous films are described, for example, in U.S. Pat. No. 7,153,569 to Kaufman, et al., as well as U.S. Application Publication Nos. 2005/0208294 to Kaufman, et al. and 2006/0149199 to Topolkaraev, et al., all of which are incorporated herein in their entirety by reference thereto for all purposes. When employed to initiate the formation of micropores, the total filler content in the film may range from about 15 wt. % to about 75 wt. %, in some embodiments, from about 20 wt. % to about 70 wt. %, and in some embodiments, from about 25 wt. % to about 65 wt. %. Likewise, the thermoplastic composition described above may constitute from about 25 wt. % to about 85 wt. %, in some embodiments, from about 30 wt. % to about 80 wt. %, and in some embodiments, from about 35 wt. % to about 75 wt. %. of the film.

When employed, the filler may include particles having any desired size, such as those having an average size of from about 0.5 to about 10 micrometers, in some embodiments, from about 1 to about 8 micrometers, and in some embodiments, from about 2 to about 6 micrometers. Suitable particles for use as a filler may include inorganic oxides, such as calcium carbonate, kaolin clay, silica, alumina, barium carbonate, sodium carbonate, titanium dioxide, zeolites, magnesium carbonate, calcium oxide, magnesium oxide, aluminum hydroxide, talc, etc.; sulfates, such as barium sulfate, magnesium sulfate, aluminum sulfate, etc.; cellulose-type powders (e.g., pulp powder, wood powder, etc.); carbon; cyclodextrins; synthetic polymers (e.g., polystyrene), and so forth. Still other suitable particles are described in U.S. Pat. Nos. 6,015,764 and 6,111,163 to McCormack, et al.; U.S. Pat. No. 5,932,497 to Morman, et al.; U.S. Pat. No. 5,695,868 to McCormack; U.S. Pat. No. 5,855,999 to McCormack, et al.; U.S. Pat. No. 5,997,981 to McCormack et al.; and U.S. Pat. No. 6,461,457 to Taylor, et al., which are incorporated herein in their entirety by reference thereto for all purposes.

Although not required, the filler may optionally be coated with a modifier (e.g., fatty acid, such as stearic acid or behenic acid) to facilitate the free flow of the particles in bulk and their ease of dispersion into the composition. Further, the filler may also be coated with a liquid additive to reduce coupling at the resin-filler interface and facilitate debonding of filler from polymer matrix during stretching. This is especially useful for the polar biodegradable polymers, which demonstrate strong interaction with fillers. Examples of such additives include surfactants, such as silicone glycol copolymers available from Dow Corning Corporation. Other suitable additives for this purpose may include titanates available from Kenrich Petrochemicals, Inc. of Bayonne, N.J. under the designations Ken-React® LICA® 01, React® LICA® 12, Ken-React® CAPOW®, Ken-React® CAPS® and zirconates available from Kenrich under the designation Ken-React® CAPS NZ 01/L. The filler may be pre-compounded with such additives before mixing with the resin, or the additives may be compounded with the resin and fillers at the melt-blending step.

In addition to the components noted above, still other additives may also be incorporated into the film of the present invention, such as melt stabilizers, processing stabilizers, heat stabilizers, light stabilizers, antioxidants, heat aging stabilizers, whitening agents, antiblocking agents, bonding agents, lubricants, colorants, etc. Phosphite stabilizers (e.g., IRGAFOS available from Ciba Specialty Chemicals of Terrytown, N.Y. and DOVERPHOS available from Dover Chemical Corp. of Dover, Ohio) are exemplary melt stabilizers. In addition, hindered amine stabilizers (e.g., CHIMASSORB available from Ciba Specialty Chemicals) are exemplary heat and light stabilizers. Further, hindered phenols are commonly used as an antioxidant in the production of films. Some suitable hindered phenols include those available from Ciba Specialty Chemicals under the trade name "Irganox®", such as Irganox® 1076, 1010, or E 201. Moreover, bonding agents may also be added to the film to facilitate bonding of the film to additional materials (e.g., nonwoven web). Examples of such bonding agents include hydrogenated hydrocarbon resins. Other suitable bonding agents are described in U.S. Pat. No. 4,789,699 to Kieffer et al. and U.S. Pat. No. 5,695,868 to McCormack, which are incorporated herein in their entirety by reference thereto for all purposes. When employed, additives (e.g., lubricant, antioxidant, stabilizer, etc.) may each be present in an amount of from about 0.001 wt. % to about 1 wt. %, in some embodiments, from about 0.005 wt. % to about 1 wt. %, and in some embodiments, from 0.01 wt. % to about 0.5 wt. % of the film.

Any known technique may be used to form a film from the compounded material, including blowing, casting, flat die extruding, etc. in one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. In yet another embodiment, however, the film is formed using a casting technique. For instance, the raw materials (e.g., starch, plant protein, plasticizer, etc.) may be supplied to a melt blending device, either separately or as a blend. The components may be separately supplied to a melt blending device where they are dispersively blended in a manner such as described above. For example, an extruder may be employed that includes feeding and venting ports. In one embodiment, the starch and plant protein may be fed to a feeding port of the twin-screw extruder and melted. Thereafter, the plasticizer may be fed into the polymer melt. Regardless, the materials are blended under high shear/pressure and heat to ensure sufficient mixing. Melt blending generally occurs at a temperature that is slightly at or above the softening point and below the decomposition temperature of the blend. For example, melt blending may occur at a temperature of from about 75° C. to about 250° C., in some embodiments, from about 80° C. to about 200° C., and in some embodiments, from about 90° C. to about 150° C. Likewise, the apparent shear rate during melt blending may range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows. Regardless of the particular manner in which it is formed, the resulting thermoplastic composition typically has an apparent viscosity of from about 20 to about 350 Pascal seconds (Pa·s), in some embodiments from about 40 to about 200 Pa·s, and in some embodiments, from about 50 to about 150 Pa·s, as determined at a temperature of 135° C. and a shear rate of 100 sec$^{-1}$.

The thickness of the resulting film may generally vary depending upon the desired use. Typically, however, the film has a thickness of about 300 micrometers or less, in some embodiments from about 5 to about 200 micrometers, in some embodiments from about 10 to about 175 micrometers, and in some embodiments, from about 20 to about 150 micrometers. Despite having such a small thickness, the film of the present invention is nevertheless able to retain good mechanical properties during use. One parameter that is indicative of the relative strength of the film is the ultimate tensile strength, which is equal to the peak stress obtained in a stress-strain curve. Desirably, the film of the present invention exhibits an ultimate tensile strength in the machine direction ("MD") of from about 1 to about 50 Megapascals (MPa), in some embodiments from about 2 to about 40 MPa, and in some embodiments, from about 5 to about 30 MPa, and an ultimate tensile strength in the cross-machine direction ("CD") of from about 1 to about 40 Megapascals (MPa), in some embodiments from about 2 to about 30 MPa, and in some embodiments, from about 5 to about 20 MPa. Although possessing good strength, it is also desirable that the film is not too stiff. One parameter that is indicative of the relative stiffness of the film (when dry) is Young's modulus of elasticity, which is equal to the ratio of the tensile stress to the tensile strain and is determined from the slope of a stress-strain curve. For example, the film typically exhibits a Young's modulus in the machine direction ("MD") of from about 50 to about 400 Megapascals ("MPa"), in some embodiments from about 75 to about 350 MPa, and in some embodiments, from about 100 to about 300 MPa, and a Young's modulus in the cross-machine direction ("CD") of from about 50 to about 350 Megapascals ("MPa"), in some embodiments from about 75 to about 300 MPa, and in some embodiments, from about 100 to about 250 MPa. The MD and/or CD peak elongation of the film, which is representative of the ductility of the film, may also be from about 50% to about 900%, in some embodiments from about 100% to about 850%, and in some embodiments, from about 150% to about 800%.

The properties of the resulting film may generally vary as desired. For example, in embodiments in which it is desired to impart breathability, the film may exhibit a water vapor transmission rate (WVTR) of about 800 grams/m$^2$-24 hours or more, in some embodiments about 1,000 grams/m$^2$-24 hours or more, in some embodiments about 1,200 grams/m$^2$-24 hours or more, and in some embodiments, from about 1,500 to about 10,000 grams/m$^2$-24 hours. The film may also limit the amount of liquid water that passes therethrough upon the application of pressure, i.e., it resists a hydrostatic pressure ("hydrohead") of about 50 millibar or more, in some embodiments about 70 millibar or more, in some embodiments about 80 millibar or more, and in some embodiments, about 100 millibar or more without allowing liquid water to pass.

If desired, the film may also be subjected to other known processes in the art, such as printing, embossing, etc.

III. Articles

The film of the present invention may be used in a wide variety of applications, such as in the packaging of items (e.g., food products, medical products, garments, garbage, absorbent articles (e.g., diapers), tissue products, etc.); absorbent articles, and so forth. In one particular embodiment, the film may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underpads, bedpads, bandages, absorbent drapes, and medical wipes; food service wipers; clothing articles; and so forth. Materials and processes suitable for forming such absorbent articles are well known to those skilled in the art. Several examples of such absorbent articles are described, for instance, in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 A1 to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes.

When incorporated into an absorbent article, it is often desired that the film is breathable. In personal care absorbent articles (e.g., diapers, feminine care pads, etc.), for instance, such breathable films may be used to form an outer cover as is known in the art. If desired, the breathable film may be laminated to a nonwoven web material formed from a wide variety of polymers as is known in the art. Polymers suitable for making nonwoven webs include, for example, polyolefins, e.g., polyethylene, polypropylene, polybutylene, and so forth; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; polyhydroxyalkanoates (e.g., polyhydroxybutyrate, polyhydroxybutyrate-co-valerate, polyhydroxybutyrate-co-hexanoate, etc.); copolymers thereof; and so forth. If desired, biodegradable polymers may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives, such as processing aids or treatment compositions to impart desired properties to the fibers, residual amounts of solvents, pigments or colorants, and so forth.

If desired, the nonwoven web material used to form the nonwoven laminate may itself have a multi-layer structure. Suitable multi-layered materials may include, for instance, spunbond/meltblown/spunbond (SMS) laminates and spunbond/meltblown (SM) laminates. Various examples of suitable SMS laminates are described in U.S. Pat. No. 4,041,203 to Brock et al.; U.S. Pat. No. 5,213,881 to Timmons, et al.; U.S. Pat. No. 5,464,688 to Timmons, et al.; U.S. Pat. No. 4,374,888 to Bornslaeger; U.S. Pat. No. 5,169,706 to Collier, et al.; and U.S. Pat. No. 4,766,029 to Brock et al., which are incorporated herein in their entirety by reference thereto for all purposes. In addition, commercially available SMS laminates may be obtained from Kimberly-Clark Corporation under the designations Spunguard® and Evolution®.

Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above.

A nonwoven web material may also contain an additional fibrous component such that it is considered a composite. For example, a nonwoven web may be entangled with another fibrous component using any of a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven fabric. Hydraulically entangled nonwoven fabrics of staple length and continuous fibers are disclosed, for example, in U.S. Pat. No. 3,494,821 to Evans and U.S. Pat. No. 4,144,370 to Boulton, which are incorporated herein in their entirety by reference thereto for all purposes. Hydraulically entangled composite nonwoven fabrics of a continuous fiber nonwoven web and a pulp layer are disclosed, for example, in U.S. Pat. No. 5,284,703 to Everhart, et al. and U.S. Pat. No. 6,315,864 to Anderson, et al., which are incorporated herein in their entirety by reference thereto for all purposes. The fibrous component of the composite may contain any desired amount of the resulting substrate. The fibrous component may contain greater than about 50% by weight of the composite, and in some embodiments, from about 60% to about 90% by weight of the composite. Likewise, the nonwoven web may contain less than about 50% by weight of the composite, and in some embodiments, from about 10% to about 40% by weight of the composite.

Although not required, the nonwoven web material may be necked or stretched in one or more directions prior to lamination to the film of the present invention. Alternatively, the nonwoven web may remain relatively inextensible in at least one direction prior to lamination to the film. In such embodiments, the nonwoven web may be optionally stretched in one or more directions subsequent to lamination to the film.

Referring to FIG. 1, one embodiment of a method for forming a laminate from a film and a nonwoven web material is shown. As shown, the raw materials may be dry mixed together (i.e., without a solvent) and added to a hopper 43 of an extruder 41. The compounded material (not shown) is supplied to an extrusion apparatus 40 and then cast into nip rolls 42 to form a single-layered precursor film 10. If a multilayer film is to be produced, the multiple layers are co-extruded together into the nip rolls 42. One or both of the rolls 42 may optionally be provided with embossing elements to impart a pattern to the film. Typically, the rolls 42 are kept at temperature sufficient to solidify and quench the film 10 as it is formed, such as from about 20 to 60° C. If desired, a vacuum box may be positioned adjacent to the rolls 42 to help keep the precursor film 10 close to the surface of the rolls 42. Additionally, air knives or electrostatic pinners may help force the precursor film 10 against the surface of the rolls 42 as it moves around a spinning roll. An air knife is a device known in the art that focuses a stream of air at a very high flow rate to pin the edges of the film.

Once cast, the precursor film 10 may then be stretched in one or more directions to form pores in the film. Although not required, the film may be stretched in-line without having to remove the film for separate processing. For example, the film may be immediately reheated to a temperature below the melting point of one or more polymers in the film, but high enough to enable the composition to be drawn or stretched. In the case of sequential orientation, the "softened" film is drawn by rolls rotating at different speeds of rotation such that the sheet is stretched to the desired draw ratio in the longitudinal direction (machine direction). This "uniaxially" stretched film may then be laminated to a fibrous web. In addition, the uniaxially stretched film may also be oriented in the cross-machine direction to form a "biaxially stretched" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

To achieve the desired breathability of the film, various parameters of the stretching operation may be selectively controlled, including the draw ratio, stretching temperature, and so forth. The draw ratio may be determined by dividing the linear speed of the film exiting the stretching operation by the linear speed of the film entering the stretching operation. In some embodiments, for example, the film is stretched in the machine direction at a draw ratio of from about 1.5 to about 10.0, in some embodiments from about 2.0 to about 6.0, and in some embodiments, from about 2.5 to about 5.0. Likewise, the film may be stretched at a temperature less than the melting temperature of the polymers contained therein, such as from about 15° C. to about 60° C., in some embodiments from about 25° C. to about 50° C., and in some embodiments, from about 30° C. to about 40° C. After stretching, the film is optionally heat-set to stabilize the stretched film. Heat-setting may be accomplished at temperatures of from about 40° C. to about 80° C., and in some embodiments, from about 50° C. to about 70° C. The heat-setting operation may reduce shrinkage of the stretched film and improve film properties and breathability. Any known in the art techniques for heat setting could be used including heated rolls and oven setting. Additional treatments may be applied to improve stretched film properties such as surface treatments, UV treatments, ultrasonic treatments, and plasma treatments.

Referring again to FIG. 1, one method for forming a uniaxially stretched film is shown. As illustrated, the precursor film 10 is directed to a film-orientation unit 44 or machine direction orienter ("MDO"), such as commercially available from Marshall and Willams, Co. of Providence, R.I. The MDO has a plurality of stretching rolls 46 (such as from five to fifteen) which progressively stretch and thin the film in the machine direction, which is the direction of travel of the film through the process as shown in FIG. 1. While the MDO 44 is illustrated with five rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 44 may act as preheat rolls. If present, these first few rolls heat the film 10 above room temperature. The progressively faster speeds of adjacent rolls in the MDO act to stretch the film 10. Likewise, if desired, one or more of the rolls of the MDO 44 may also act as heat setting rolls.

A nonwoven web is also employed for laminating to the stretched film 10. For example, the nonwoven web may simply be unwound from a supply roll. Alternatively, as shown in FIG. 1, a nonwoven web 30 may be formed in-line, such as by dispensing polymer filaments 50 from a pair of spinnerettes 48 onto a conveyor assembly 52 to form mat 54. The filaments 50 of mat 54 are then compressed to form inter-filament bonding using a pair of nip rollers 56, resulting in the spunbonded web 30. If desired, a vacuum (not shown) may be utilized to maintain the fibers on the conveyor assembly. Following compaction, the nonwoven web 30 is directed to a nip defined between rolls 58 for laminating to the film 10.

Various techniques may be utilized to bond the film 10 to the nonwoven web 30, including adhesive bonding, such as through slot or spray adhesive systems; thermal bonding; ultrasonic bonding; microwave bonding; extrusion coating; and so forth. Examples of suitable adhesives that may be used in the present invention include Rextac 2730 and 2723 available from Huntsman Polymers of Houston, Tex., as well as adhesives available from Bostik Findley, Inc, of Wauwatosa, Wis. The basis weight of the adhesive may be between about 1.0 and 3.0 grams per square meter. The type and basis weight of the adhesive used will be determined on the attributes desired in the final laminate and end use. Although not required, the adhesive may be applied directly to the nonwoven web prior to lamination with the film. Further, to achieve improved drape, the adhesive may be applied in a pattern. In FIG. 1, the film 10 is simultaneously bonded on its other side to a second material 30a originating from a supply roll 62. The second material 30a may be a second nonwoven web, or another film layer. The resulting laminate 32 is wound and stored on a supply roll 60. If desired, the laminate 32 may also be optionally stretched in the cross-machine and/or machine directions to enhance its extensibility.

The present invention may be better understood with reference to the following examples.

Test Methods

Apparent Melt Viscosity:

The rheological properties of polymer samples were determined using a Göttfert Rheograph 2003 capillary rheometer with WinRHEO version 2.31 analysis software. The setup included a 2000-bar pressure transducer and a 30/1:0/180 roundhole capillary die. Sample loading was done by alternating between sample addition and packing with a ramrod. A 2-minute melt time preceded each test to allow the polymer to completely melt at a test temperature (135° C.). The capillary rheometer determined the apparent melt viscosity (Pa·s) at various shear rates, such as 100, 200, 500, 1000, 2000, and 4000 $s^{-1}$. The resultant rheology curve of apparent shear rate versus apparent melt viscosity gave an indication of how the polymer would run at that temperature in an extrusion process.

Tensile Properties:

The strip tensile strength values were determined in substantial accordance with ASTM Standard D638-99. A constant-rate-of-extension type of tensile tester was employed. The tensile testing system was a Sintech 1/D tensile tester, which is available from Sintech Corp. of Cary, N.C. The tensile tester was equipped with TESTWORKS 4.08B software from MTS Corporation to support the testing. An appropriate load cell was selected so that the tested value fell within the range of 10-90% of the full scale load. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of abut 127 millimeters per minute until breakage occurred. The modulus, peak stress, and strain at break (peak elongation) were measured in the machine direction ("MD") and cross-machine directions ("CD").

Example 1

100 wt. % Pro-Cote® 4200 (DuPont) was initially added to a K-Tron feeder (K-Tron America, Pitman, N.J.) that fed the materials into a ZSK-30 co-rotating, twin screw extruder (Werner and Pfleidere Corporation, Ramsey, N.J.). Pro-Cote® 4200 is a soy protein having a weight average molecular weight of about 150,000 to 200,000 Daltons. The extruder diameter was 30 mm and the length of the screws was up to 1328 mm. The extruder has 14 barrels, numbered consecutively 1 to 14 from the feed hopper to the die. The first barrel received the soy protein at a feed rate of 10 lbs/hr. The temperature profile of zones 1 to 14 of the extruder was 100-130° C. for each zone. The screw speed was set at 110 rpm to achieve a torque of 40%. The melt temperature was 123° C. Glycerin was pumped into barrel 5 with a pressurized injector connected with an Eldex pump (Napa, Calif.) at a rate of 24 grams per minute to achieve a 30 wt. % concentration. The vent was opened at the end of the extruder to release moisture. A die was employed to form strands that had 2 openings of 7 mm in diameter, which were separated by 13 mm. The strands were brown in color, uneven, and appeared to have some unconverted material.

Example 2

A mixture of 80 wt. % Glucosol™ 800 (Chemstar, Minneapolis, Minn.) and 20 wt. % Pro-Cote® 4200 (DuPont) was initially formed in a Hobart mixer. Glucosol™ 800 is a modified starch having a weight average molecular weight (determined by GPC) of 2,900,000; polydispersity index of about 28; bulk density of 30~40 lbs/ft$^3$, and $D_{98}$ particle size of 140 mesh. The mixture was then added to a K-Tron feeder (K-Tron America, Pitman, N.J.) that fed the materials into a ZSK-30 co-rotating, twin screw extruder (Werner and Pfleidere Corporation, Ramsey, N.J.) as described in Example 1. The first barrel received the mixture of starch and soy at a feed rate of 10 lbs/hr. The temperature profile of zones 1 to 14 of the extruder was 90° C., 110° C., 125° C., 130° C., 130° C., 122° C., and 117° C. The screw speed was set at 150 rpm to achieve a torque of about 60%. The melt temperature was 128° C. to 130° C. Glycerin was pumped into barrel 5 with a pressurized injector connected with an Eldex pump (Napa, Calif.) at a rate of 24 grams per minute to achieve a 30 wt. % concentration. The vent was opened at the end of the extruder to release moisture. A die was employed to form strands that had 2 openings of 7 mm in diameter, which were separated by 13 mm. The strands were smooth and light brown in color. Once formed, the strands were cooled on a conveyer belt and then pelletized.

Example 3

A mixture of 60 wt. % Glucosol™800 (Chemstar, Minneapolis, Minn.) and 40 wt. % Pro-Cote® 4200 (DuPont) was initially formed in a Hobart mixer and then added to a K-Tron feeder (K-Tron America, Pitman, N.J.) that fed the materials into a ZSK-30 co-rotating, twin screw extruder (Werner and Pfleidere Corporation, Ramsey, N.J.) as described in Example 1. The first barrel received the mixture of starch and soy at a feed rate of 10 lbs/hr. The temperature profile of zones 1 to 14 of the extruder was 90° C., 110° C., 118° C., 122° C., 122° C., 122° C., and 115° C. The screw speed was set at 150 rpm to achieve a torque of about 60% to 68%. The melt temperature was 124° C. to 127° C. Glycerin was pumped into barrel 5 with a pressurized injector connected with an Eldex pump (Napa, Calif.) at a rate of 24 grams per minute to achieve a 30 wt. % concentration. The vent was opened at the end of the extruder to release moisture. A die was employed to form strands that had 2 openings of 7 mm in diameter, which were separated by 13 mm. The strands were smooth and brown in color. Once formed, the strands were cooled on a conveyer belt and then pelletized.

Example 4

A mixture of 60 wt. % Glucosol™ 800 (Chemstar, Minneapolis, Minn.), 20 wt. % Pro-Cote® 4200 (DuPont), and 20 wt. % wheat gluten (ADM, Decatur, Ill.) was formed in a Hobart mixer. Wheat gluten is composed of the water-insoluble prolamin and glutelin protein fractions known as gliadin and glutenin, respectively. The molecular weight of gliadin is in the range of 20,000 to 50,000 Daltons, while the molecular weight of glutenin is about 250,000 Daltons. The mixture was added to a K-Tron feeder (K-Tron America, Pitman, N.J.) that fed the materials into a ZSK-30 co-rotating, twin screw extruder (Werner and Pfleidere Corporation, Ramsey, N.J.) as described in Example 1. The first barrel received the mixture of starch and soy at a feed rate of 10 lbs/hr. The temperature profile of zones 1 to 14 of the extruder was 90° C., 110° C., 115° C., 118° C., 118° C., 118° C., and 115° C. The screw speed was set at 150 rpm to achieve a torque of about 63% to 67%. The melt temperature was 124° C. to 127° C. Glycerin was pumped into barrel 5 with a pressurized injector connected with an Eldex pump (Napa, Calif.) at a rate of 24 grams per minute to achieve a 30 wt. % concentration. The vent was opened at the end of the extruder to release moisture. A die was employed to form strands that had 2 openings of 7 mm in diameter, which were separated by 13 mm. The strands were smooth and dark brown in color. Once formed, the strands were cooled on a conveyer belt and then pelletized.

Examples 5-7

Mixtures of Glucosol™ 800 (Chemstar, Minneapolis, Minn.) and wheat gluten (Meelunie America, Inc., Farmington, Mich.) were blended in a Hobart mixer according to the ratios indicated below in Table 1. In addition, 2 wt. % Excel P-40S (Kao Corporation, High Point, N.J.) was also added to the mixture. The ingredients were mixed for about 5 minutes. The mixture was then added to K-Tron feeder (K-Tron America, Pitman, N.J.) that fed the materials into a ZSK-30 extruder (Werner and Pfleidere Corporation, Ramsey, N.J.) as described in Example 1. The first barrel received the mixture at 10 lbs/hr and the extruder was heated to a temperature profile as shown in Table 1. Glycerin was pumped into barrel 5 with a pressurized injector connected with an Eldex pump (Napa, Calif.) at a rate of 2.5 pounds per hour to achieve a 20 wt. % concentration. The vent was opened at the end of the extruder to release moisture. A die was employed to form strands that had 2 openings of 7 mm in diameter, which were separated by 13 mm. Once formed, the strands were cooled on a conveyer belt and then pelletized.

TABLE 1

Processing Conditions

| Sample No. | Starch/Gluten Ratio | Mixture Feeding Rate (lb/hr) | Glycerin (lb/hr) | Extruder Speed (rpm) | Extruder Temperature Profile (° C.) | | | | | | | | $P_{melt}$ (psi) | Torque (%) |
|---|---|---|---|---|---|---|---|---|---|---|---|---|---|---|
| | | | | | $T_1$ | $T_2$ | $T_3$ | $T_4$ | $T_5$ | $T_6$ | $T_7$ | $T_{melt}$ | | |
| Example 5 | 80/20 | 10 | 2.5 | 150 | 90 | 105 | 120 | 125 | 125 | 124 | 124 | 133 | 110~160 | 45~50 |
| Example 6 | 70/30 | 10 | 2.5 | 150 | 90 | 101 | 120 | 125 | 125 | 120 | 118 | 122 | 100~140 | 35~40 |
| Example 7 | 60/40 | 10 | 2.5 | 150 | 90 | 104 | 123 | 122 | 129 | 115 | 116 | 120 | 120~200 | 35~38 | form strands that had 2 openings of 7 mm in diameter, which were separated by 13 mm. The strands were smooth and brown in color. Once formed, the strands were cooled on a conveyer belt and then pelletized.

Figure 2:
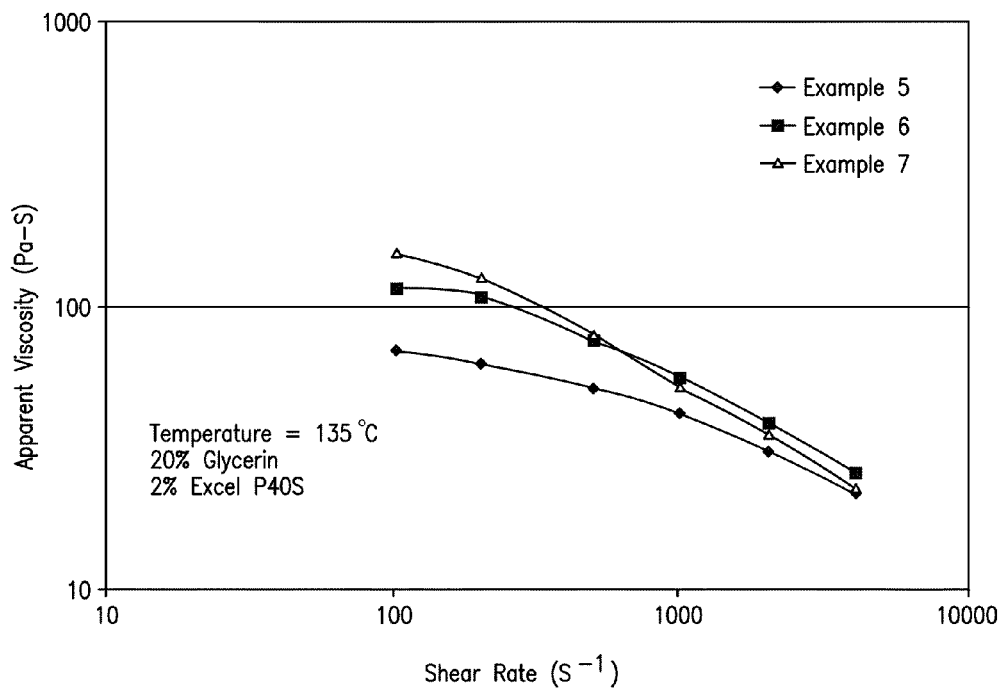
FIG. 2 is a graphical representation of the apparent melt viscosity (Pa-s) of the samples of Examples 5-7 versus shear rate ($s^{-1}$)
Figure 3:
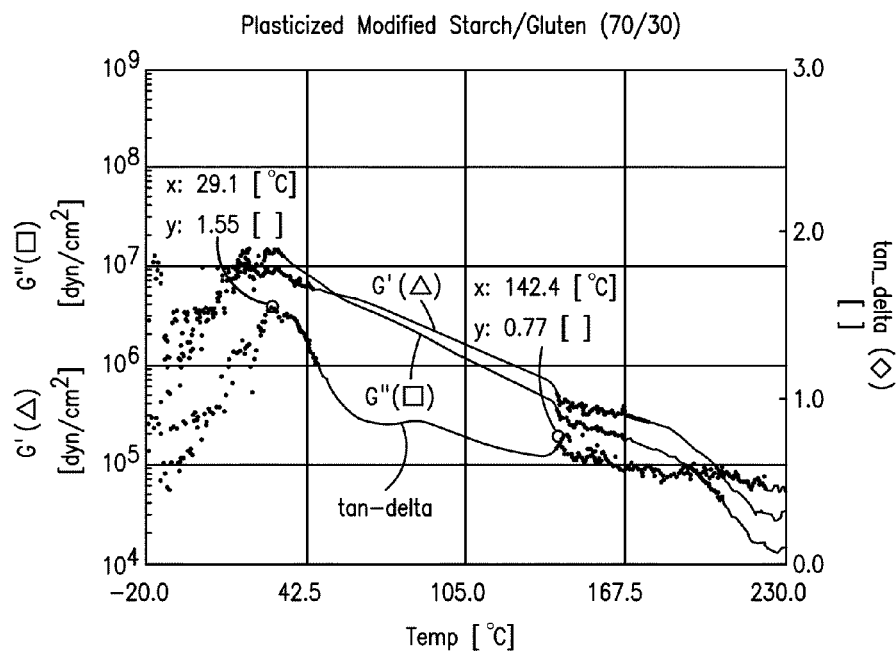
FIG. 3 is a graphical representation of the glass transition temperature and melting temperature for the sample of Example 6.

Samples were tested for their melt rheology behaviors as described above. The results are shown in FIG. 2. As indicated, the apparent viscosity increased (at the same shear rate) as the percentage of gluten protein increased and the percentage of starch decreased. A sample from Example 6 was also tested for its glass transition and melting temperatures using AIRES (Advanced Rheometric Expansion System), manufactured by Rhemetric Scientific (Piscataway, N.J.). The glass transition temperature, $T_g$, storage modulus, G', and loss modulus, G", were determined by peak tan ($\delta$) in the temperature ramp. The measurements were conducted in a dynamic mode. The following test conditions were used: frequency was 6.28 rad/sec, heating rate was 3° C./min, strain of 1%, and test fixture of 8 mm and 25 mm parallel plates. FIG. 3 represents the results from the dynamic mechanical testing. As indicated, $T_g$ for the sample was about 29° C. and the melting temperature was about 142.4° C. The factors affecting the storage modulus, G', may be the molecular weight of base materials, level of mixing during processing of thermoplastic modified starch and gluten.

Example 8

ECOFLEX® F BX7011 (polybutylene adipate terephthalate, BASF) was added to a K-Tron feeder (K-Tron America, Pitman, N.J.) that fed vertically into a ZSK-30 extruder (Werner and Pfleidere Corporation, Ramsey, N.J.), such as described in Example 1. The first barrel received the resin at 15 lbs/hr when the extruder was heated to the temperature profile of 130° C., 140° C., 150° C., 155° C., 155° C., 145° C., and 140° C., from zones 1 to 7, and the screw was set to rotate at 150 rpm. "2sst" calcium carbonate (Omya, Inc. of Alpharetta, Ga.) was also added to the extruder at a concentration of 50 wt. %. The melting temperature was 160° C., the torque was about 80 to 90%, and the pressure was about 420 to 460 psi. The vent was closed at the end of the extruder without a need of releasing moisture. A 3-hole die was used to shape the melt into strands that were cooled on a conveyer belt and then pelletized for dry blending.

Example 9

70 wt. % ECOPOL™ EBP 203 resin (polyethylene adipate isophthalate, Econeer Co., Ltd.) was dry blended with 30 wt. % of the thermoplastic starch/gluten mixture from Example 6 using a Rheomex 252 single screw extruder and cast into a film. The processing temperatures from zone 1 to 5 were 120° C., 130° C., 140° C., 140° C. (pump), and 130° C. (die). The melt temperature was 141° C. and the die gap was 20 mils. The pellet feeding rate was set at 70 rpm, with the torque fluctuating within 700~800 m-g. The pressure at the die was about 2050 psi. The film thickness ranged from 4 to 5 mils. The film surface was observed to be relatively rough and weak.

Example 10

70 wt. % ECOFLEX® F BX 7011 resin was dry blended with 30 wt. % of the thermoplastic starch/gluten mixture from Example 6 using a Rheomex 252 single screw extruder and cast into a film. The processing temperatures from zone 1 to 5 were 135° C., 140° C., 140° C., 140° C. (pump), and 140° C. (die). The melt temperature was 157° C. and the die gap was 20 mils. The pellet feeding rate was set at 60 rpm, with the torque fluctuating within 2400~2500 m-g. The pressure at the die was about 2400 psi. The film thickness ranged from 2 to 5 mils. The film surface was observed to be extremely soft and flexible.

Example 11

60 wt. % ECOFLEX® F BX 7011 resin was dry blended with 40 wt. % of the thermoplastic starch/gluten mixture from Example 6 using a Rheomex 252 single screw extruder and cast into a film. The processing temperatures from zone 1 to 5 were 135° C., 140° C., 140° C., 140° C. (pump), and 140° C. (die). The melt temperature was 155° C. and the die gap was 20 mils. The pellet feeding rate was set at 60 rpm, with the torque fluctuating within 2000~2100 m-g. The pressure at the die was about 2900 psi. The film thickness ranged from 2 to 5 mils. The film surface was observed to be soft and flexible.

Example 12

60 wt. % ECOFLEX® F BX 7011 resin was dry blended with 40 wt. % of the thermoplastic starch/gluten mixture from Example 6 using a Rheomex 252 single screw extruder and cast into a film. The processing temperatures from zone 1 to 5 were 135° C., 140° C., 140° C., 140° C. (pump), and 140° C. (die). The melt temperature was 156° C. and the die gap was 20 mils. The pellet feeding rate was set at 60 rpm, with the torque fluctuating within 1600~1700 m-g. The pressure at the die was about 2150 psi. The film thickness ranged from 2 to 5 mils. The film surface was observed to be rigid.

Example 13

The filled ECOFLEX® F BX 7011 resin from Example 8 and the thermoplastic modified starch/gluten from Example 6 (50/50 ratio) were dry blended for film casting using Rheomex 252 single screw extruder. The resulted film contained 25 wt. % 2-sst $CaCO_3$ filler, 15 wt. % thermoplastic modified starch/gluten, and 60 wt. % ECOFLEX® F BX 7011. The processing temperatures from zone 1 to 5 were 135° C., 140° C., 140° C., 140° C. (pump), and 140° C. (die). The melt temperature was 157° C. and the die gap was 20 mils. The pellet feeding rate was set at 60 rpm, with the torque fluctuating within 4300~4400 m-g. The pressure at the die was about 5600 psi. The film thickness was 2 mils.

Example 14

The filled ECOFLEX® F BX 7011 resin from Example 8 and the thermoplastic modified starch/gluten from Example 6 (70/30 ratio) were dry blended for film casting using Rheomex 252 single screw extruder. The resulted film contained 15 wt. % 2-sst $CaCO_3$ filler, 28 wt. % thermoplastic modified starch/gluten, and 57 wt. % ECOFLEX® F BX 7011. The processing temperatures from zone 1 to 5 were 135° C., 140° C., 140° C., 140° C. (pump), and 140° C. melt temperature was 156° C. and the die gap was 20 mils. The pellet feeding rate was set at 60 rpm, with the torque fluctuating within 4000~4200 m-g. The pressure at the die was about 5400 psi. The film thickness was 2 mils.

The mechanical properties of the films of Examples 9-14 were determined as described above. The results are shown below in Table 2.

TABLE 2

| | | | Thickness (mil) | | Peak Stress (MPa) | | Strain at Break (%) | | Modulus (MPa) | |
|---|---|---|---|---|---|---|---|---|---|---|
| | Sample No. | | MD | CD | MD | CD | MD | CD | MD | CD |
| Dogbone | Example 9 | Mean | 4.44 | 4.18 | 7 | 4 | 45 | 12 | 252 | 166 |
| | Example 10 | | 3.08 | 2.68 | 21 | 12 | 639 | 538 | 106 | 115 |
| | Example 10 | | 5.68 | 5.88 | 21 | 13 | 755 | 597 | 110 | 115 |
| | Example 11 | | 2.22 | 2.28 | 16 | 7 | 485 | 365 | 107 | 133 |
| | Example 11 | | 4.78 | 4.74 | 19 | 8 | 692 | 382 | 116 | 108 |
| | Example 12 | | 2.38 | 2.36 | 10 | 4 | 378 | 22 | 109 | 112 |
| | Example 12 | | 5.64 | 5.64 | 8 | 4 | 410 | 9 | 111 | 105 |
| | Example 13 | | 3.02 | 2.78 | 8 | 7 | 176 | 342 | 131 | 139 |
| | Example 14 | | 2.36 | 2.44 | 12 | 6 | 323 | 229 | 131 | 133 |

The elongation for Examples 10 and 11 was determined to be close to the elongation of a 100% ECOFLEX® F BX 7011 film. However, the film peak stress was relatively low. When ECOFLEX® F BX 7011 is a minor in the blend shown in Example 12, the elongation decreased significantly. The film modulus values were moderate.

Example 15

To evaluate breathability, three (3) film samples made according to Example 14 and stretched under ambient conditions in the machine direction 0%, 100%, and 150%, respectively. The film breathability was then tested according to ASTM 3806 for MOCON. The results show that an unstretched film exhibited a breathability of about 900 MOCON, while the films stretched to 100% and 150% exhibited breathabilities of 1270 and 1280 MOCON, respectively.

Example 16

Figure 4:
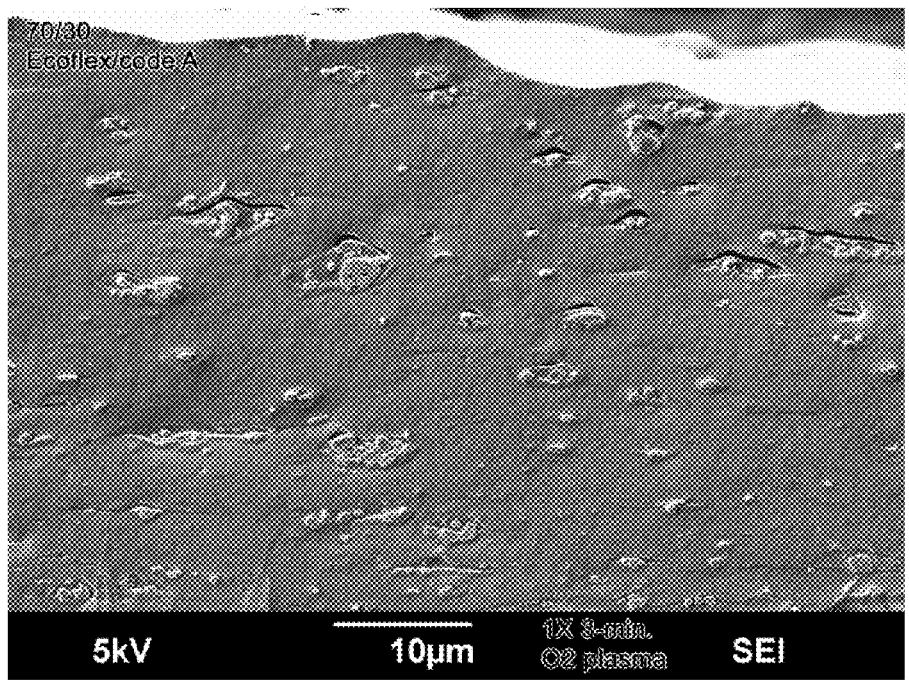
FIG. 4 is a scanning electron microscopy (SEM) photograph of the film of Example 10 (5 kV, 1×)
Figure 5:
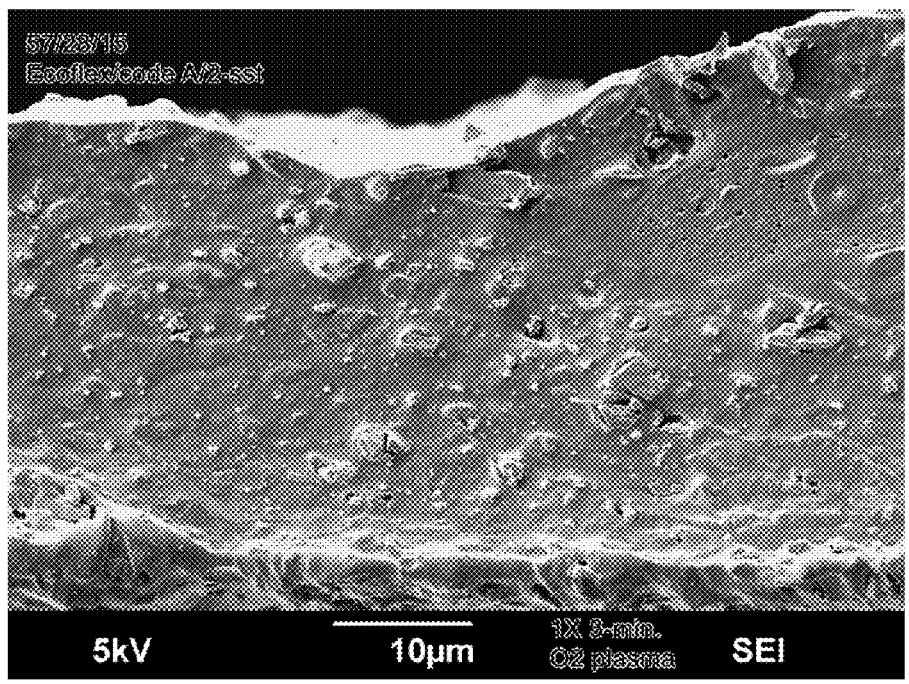
FIG. 5 is a scanning electron microscopy (SEM) photograph of the film of Example 15 (5 kV, 1×).

A scanning electron microscopy (SEM) photographs (magnification of 1900×) were taken of the film of Examples 10 and 15. The photographs were obtained by plasma etching/optical method using the standard secondary electron imaging mode achieved by a positive-biased Everhart-Thornley detector. The results for Examples 10 and 15 are shown in FIGS. 4 and 5, respectively. In FIG. 5, the film cross-sectional profile was fully filled due to the presence of ECOFLEX® F BX 7011. When 2-sst $CaCO_3$ was added into the blend, the film breathability increased about 42% although the film debonding was not visibly seen.

Example 17

Wheat gluten (80%, Meelunie America, Inc.) was blended with different plasticizers on a HAAKE Rheomix 300 (69 $cm^3$) benchtop mixer with cam rotors. All of the experiments were conducted at 100 RPM and 60° C. with a 50 gram sample. The plasticizers used were glycerol (pH=6) and lactic acid (pH=2.4) at a 30% addition level. The gluten moisture content out of the bag was about 6.0% and the gluten was also dried to about 3% using an oven at 80° C. with dessicant. To produce the samples, the gluten and plasticizer were pre-measured and then the gluten was added to the mixer. Thereafter, the plasticizer was added. The melt temperature and torque were continually monitored during mixing and mixing was stopped approximately five minutes after the maximum torque was reached. The sample was scraped out of the mixer and placed in a glass sample jar. The results are set forth below in Table 3.

TABLE 3

Processing Conditions

| Plasticizer (%) | Gluten Moisture (%) | Set Temp (° C.) | Melt Temp (° C.) | Torque (m-g) |
|---|---|---|---|---|
| Glycerol (30%) | 5.85% - out of bag | 60 | 103 | 1300 |
| Glycerol (30%) | 3% - dried in oven | 60 | 120 | 1750 |
| Lactic Acid (30%) | 5.85% - out of bag | 60 | 90 | 1200 |
| Lactic Acid (30%) | 3% - dried in oven | 60 | 98 | 1600 |

As indicated, the melt temperature and torque increased when glycerol was used as the plasticizer. This was most likely due to the disulfide bond formation and aggregation, which raises the viscosity of the blend causing additional shear heat introduced into blend.

Example 18

25 wt. % vital wheat gluten (80%, Meelunie America, Inc.); 70 wt. % ECOFLEX® F BX 7011 (polybutylene adipate terephthalate, BASF); and 5 wt. % plasticizer (both lactic acid and glycerol plasticizers were tested) were used to form strands. More specifically, the wheat gluten and copolyester were initially added to a K-Tron feeder (K-Tron America, Pitman, N.J.) that fed the materials into zone 2 of a ZSK-30 co-rotating, twin screw extruder (Werner and Pfleidere Corporation, Ramsey, N.J.). The temperature profile of zone 1 was set to 90° C. and zones 2-7 were set at 120° C. Once system was stabilized, the temperatures were dropped to about 100° C. The plasticizer was pumped into barrel 5 with a pressurized injector connected with an Eldex pump (Napa, Calif.) at a rate of 7.2 grams per minute to achieve a 5 wt. % concentration. Both lactic acid and glycerol plasticizers were tested. While the material was being extruded, the melt temperature, pressure and torque were monitored. The melt temperature remained steady at 100° C.; the melt pressure remained between 40-50 psi, and the torque remained at 38-41 motor load percent. A die was employed to form strands that had 2 openings of 7 mm in diameter, which were separated by 13 mm. For each of tests run, the resulting strands were filled with voids.

Example 19

25 wt. % vital wheat gluten (80%, Meelunie America, Inc.); 70 wt. % GSPIa AD92 (polybutylene succinate, Mitsubishi); and 5 wt. % plasticizer (both lactic acid and glycerol plasticizers were tested) were used to form strands. More specifically, the wheat gluten and polybutylene succinate were initially added to a K-Tron feeder (K-Tron America, Pitman, N.J.) that fed the materials into zone 2 of a ZSK-30 co-rotating, twin screw extruder (Werner and Pfleidere Corporation, Ramsey, N.J.). The temperature profile of zone 1 was set to 90° C. and zones 2-7 were set at 120° C. Once system was stabilized, the temperatures were dropped to about 100° C. The plasticizer was pumped into barrel 5 with a pressurized injector connected with an Eldex pump (Napa, Calif.) at a rate of 7.2 grams per minute to achieve a 5 wt. % concentration. While the material was being extruded, the melt temperature, pressure and torque were monitored. The melt temperature remained steady at 100° C.; the melt pressure remained between 40-50 psi, and the torque remained at 38-41 motor load percent. A die was employed to form strands that had 2 openings of 7 mm in diameter, which were separated by 13 mm. For each of tests run, the resulting strands were filled with voids.

Example 20

25 wt. % vital wheat gluten (80%, Meelunie America, Inc.); 70 wt. % HS101A (starch blend, Evergreen); and 5 wt. % plasticizer (both lactic acid and glycerol plasticizers were tested) were used to form strands. More specifically, the wheat gluten and starch blend were initially added to a K-Tron feeder (K-Tron America, Pitman, N.J.) that fed the materials into zone 2 of a ZSK-30 co-rotating, twin screw extruder (Werner and Pfleidere Corporation, Ramsey, N.J.). The temperature profile of zone 1 was set to 90° C. and zones 2-7 were set at 120° C. Once system was stabilized, the temperatures were dropped to about 100° C. The plasticizer was pumped into barrel 5 with a pressurized injector connected with an Eldex pump (Napa, Calif.) at a rate of 7.2 grams per minute to achieve a 5 wt. % concentration. While the material was being extruded, the melt temperature, pressure and torque were monitored. The melt temperature remained steady at 100° C.; the melt pressure remained between 40-50 psi, and the torque remained at 38-41 motor load percent. A die was employed to form strands that had 2 openings of 7 mm in diameter, which were separated by 13 mm. For each of tests run, the resulting strands were filled with voids.

Example 21

100 wt. % Vital wheat gluten (80%, Meelunie America, Inc.) was initially added to a gravimetric feeder that fed the materials into the throat of a Thermo 17 mm twin screw extruder. A flat temperature profile of 60° C. and a screw speed of 100 rpm were utilized. Glycerol was pumped into zone 2 of the extruder to achieve a 30 wt. % concentration. A die was employed to form strands that had 1 opening of 3 mm in diameter. Initial plasticization was not successful due to crosslinking within the extruder after the second set of kneading blocks of the screw. Additional tests were performed that used Excel P-40S (Kao Corporation, High Point, N.J.) at a level of 1%. Although plasticized gluten was obtained from the die, it was not well formed and was crumbly.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A biodegradable and renewable film comprising a thermoplastic composition, wherein the thermoplastic composition contains a starch component in an amount from about 30 wt. % to about 80 wt. %, a plant protein component in an amount from about 10 wt. % to about 40 wt. %, and a plasticizer component in an amount from about 10 wt. % to about 40 wt. %, and a biodegradable polyester selected from the group consisting of polycaprolactone, polyesteramides, modified polyethylene terephthalate, polylactic acid and copolymers and terpolymers thereof, polyglycolic acid, polyalkylene carbonates, succinate-based aliphatic polymers, aliphatic-aromatic copolyesters, and combinations thereof, further wherein the combined amount of the starch and the plant protein components in the thermoplastic composition is about 40 wt. % or greater, wherein the film exhibits a peak elongation of from about from about 50% to about 900% at a strain rate of about 127 millimeters per minute in the machine direction.

2. The film of claim 1, wherein the starch component includes a chemically modified starch.

3. The film of claim 1, wherein the plant protein component includes zein, corn gluten, wheat gluten, canola, sunflower, sorghum, soy, a derivative thereof, or a combination thereof.

4. The film of claim 1, wherein the plant protein component includes gluten or a derivative thereof.

5. The film of claim 4, wherein the plasticizer component includes at least one plasticizer having a pH of from about 1 to about 5.

6. The film of claim 5, wherein the plasticizer includes a carboxylic acid.

7. The film of claim 1, wherein the plant protein component includes soy protein or a derivative thereof.

8. The film of claim 7, wherein the plasticizer component includes a polyol.

9. The film of claim 1, wherein the plant protein component contains about 75 wt. % or more of protein.

10. The film of claim 1, wherein the combined amount of the starch and the plant protein components in the thermoplastic composition is from about 60 wt. % to about 90 wt. %.

11. The film of claim 1, wherein the starch component constitutes from about 40 wt. % to about 70 wt. % of the thermoplastic composition.

12. The film of claim 1, wherein the plant protein component constitutes from about 15 wt. % to about 35 wt. % of the thermoplastic composition.

13. The film of claim 1, wherein the plasticizer component constitutes from about 15 wt. % to about 35 wt. % of the thermoplastic composition.

14. The film of claim 1, wherein the biodegradable polyester includes an aliphatic-aromatic copolyester.

15. The film of claim 1, wherein the film is microporous.

16. The film of claim 15, wherein the film contains a filler and is stretched.

17. The film of claim 15, wherein the film has a water vapor transmission rate of about 1,000 grams/m$^2$-24 hours or more.

18. The film of claim 1, wherein the film has a thickness of from about 5 to about 200 micrometers.

19. A laminate comprising:
a nonwoven web material; and
a film joined to the nonwoven web material, wherein the film comprises a thermoplastic composition, wherein the thermoplastic composition contains a starch component in an amount from about 30 wt. % to about 80 wt. %, a plant protein component in an amount from about 10 wt. % to about 40 wt. %, and a plasticizer component in an amount from about 10 wt. % to about 40 wt. %, and a biodegradable polyester selected from the group consisting of polycaprolactone, polyesteramides, modified polyethylene terephthalate, polylactic acid and copolymers and terpolymers thereof, polyglycolic acid, polyalkylene carbonates, succinate-based aliphatic polymers, aliphatic-aromatic copolyesters, and combinations thereof, further wherein the combined amount of the starch and the plant protein components in the thermoplastic composition is about 40 wt. % or greater, wherein the film exhibits a peak elongation of from about from about 50% to about 900% at a strain rate of about 127 millimeters per minute in the machine direction.

20. An absorbent article comprising a generally liquid-impermeable, vapor-permeable layer, the layer comprising a microporous film that includes a thermoplastic composition, wherein the thermoplastic composition contains a starch component in an amount from about 30 wt. % to about 80 wt. %, a plant protein component in an amount from about 10 wt. % to about 40 wt. %, and a plasticizer component in an amount from about 10 wt. % to about 40 wt. %, and a biodegradable polyester selected from the group consisting of polycaprolactone, polyesteramides, modified polyethylene terephthalate, polylactic acid and copolymers and terpolymers thereof, polyglycolic acid, polyalkylene carbonates, succinate-based aliphatic polymers, aliphatic-aromatic copolyesters, and combinations thereof, further wherein the combined amount of the starch and the plant protein components in the thermoplastic composition is about 40 wt. % or greater, wherein the film exhibits a peak elongation of from about from about 50% to about 900% at a strain rate of about 127 millimeters per minute in the machine direction.

21. The absorbent article of claim 20, further comprising an absorbent core positioned between the generally liquid-impermeable, vapor-permeable layer and a liquid-permeable layer.

22. The absorbent article of claim 20, wherein the microporous film is joined to a nonwoven web material.

23. The absorbent article of claim 20, wherein the microporous film has a water vapor transmission rate of about 1,000 grams/m$^2$-24 hours or more.

24. A method for forming a biodegradable and renewable film, the method comprising:
melt blending a composition that comprises a starch component in an amount from about 30 wt. % to about 80 wt. %, a plant protein component in an amount from about 10 wt. % to about 40 wt. %, and a plasticizer component in an amount from about 10 wt. % to about 40 wt. %, and a biodegradable polyester selected from the group consisting of polycaprolactone, polyesteramides, modified polyethylene terephthalate, polylactic acid and copolymers and terpolymers thereof, polyglycolic acid, polyalkylene carbonates, succinate-based aliphatic polymers, aliphatic-aromatic copolyesters, and combinations thereof, further wherein the combined amount of the starch and the plant protein components in the composition is about 40 wt. % or greater; and
extruding the composition onto a surface to form a film, wherein the film exhibits a peak elongation of from about from about 50% to about 900% at a strain rate of about 127 millimeters per minute in the machine direction.

25. The method of claim 24, wherein melt blending occurs at a temperature of from about 75° C. to about 250° C.

26. The method of claim 24, further comprising stretching the film in the machine direction, cross-machine direction, or both.

27. The method of claim 26, wherein the stretched film is microporous.

28. The film of claim 1, wherein the film exhibits a peak elongation of from about from about 150% to about 800% at a strain rate of about 127 millimeters per minute in the machine direction.

29. The film of claim 1, wherein the film exhibits a peak elongation of from about from about 50% to about 900% at a strain rate of about 127 millimeters per minute in the cross-machine direction.

30. The film of claim 1, wherein the film exhibits a Young's modulus in the machine direction of from about from about 100 to about 300 Megapascals.

* * * * *